United States Patent [19]
Murray et al.

[11] 3,965,490
[45] June 29, 1976

[54] FEMORAL INSERT FOR HIP JOINT PROSTHESIS

[75] Inventors: Ian P. Murray, Hewitt; Mark R. Forte, Pinebrook, both of N.J.

[73] Assignee: Howmedica, Inc., New York, N.Y.

[22] Filed: Oct. 6, 1975

[21] Appl. No.: 619,622

Related U.S. Application Data

[63] Continuation-in-part of Ser. No. 523,926, Nov. 14, 1974, abandoned.

[52] U.S. Cl. .............................. 3/1.913; 128/92 CA
[51] Int. Cl.² ........................................... A61F 1/24
[58] Field of Search ............................ 3/1.9–1.913, 3/1; 128/92 CA, 92 C

[56] References Cited
UNITED STATES PATENTS

| | | | |
|---|---|---|---|
| 3,694,820 | 10/1972 | Scales et al. .................. | 128/92 C X |
| 3,744,061 | 7/1973 | Frost ..................................... | 3/1.912 |

FOREIGN PATENTS OR APPLICATIONS

| | | | |
|---|---|---|---|
| 1,448,955 | 7/1966 | France ........................... | 128/92 CA |
| 1,046,516 | 7/1953 | France ........................... | 128/92 CA |

OTHER PUBLICATIONS

F. R. Thompson Hip Prosthesis, Villalium Surgical Appliances (Catalog), Austenal Co., Howmet Corp., New York, N.Y. 1964, p. 23.

Trapezoidal–28 Total Hip Prosthesis– Zimmer catalog, Warsaw, Ind., Sept. 1964, pp. A14–1 and A14–2.
The Eicher Hip Prosthesis, Catalog No. 6827, Catalog of Vitallium Surgical Appliances, 1959, p. 8.
Eicher Hip Prostheses–No. 6927, Vilallium Surgical Appliances, (Catalog), Austenal Co., Howmet Corp., New York, N.Y. 1964, p. 26.

*Primary Examiner*—Ronald L. Frinks
*Attorney, Agent, or Firm*—Connolly and Hutz

[57] ABSTRACT

A polished spherical head is connected to a proximally curved longitudinally tapered stem by a neck and collar. The overall length is about 6 inches or 150 mm. with the stem being approximately 4½ inches or 115 mm. long. The stem has substantially flattened ellipsoidal cross section tapering from a relatively high curved proximal portion to a smooth junction with the distal portion which more gradually tapers in height to a rounded end. The thickness of the stem tapers uniformly from the proximal to distal end. One or more shallow teardrop-shaped depressions are disposed in the flat sides of the curved proximal portion of the stem with their bases disposed substantially parallel to each other at a distance apart which smoothly merges into a junction with the outsides of the distal portion.

28 Claims, 13 Drawing Figures

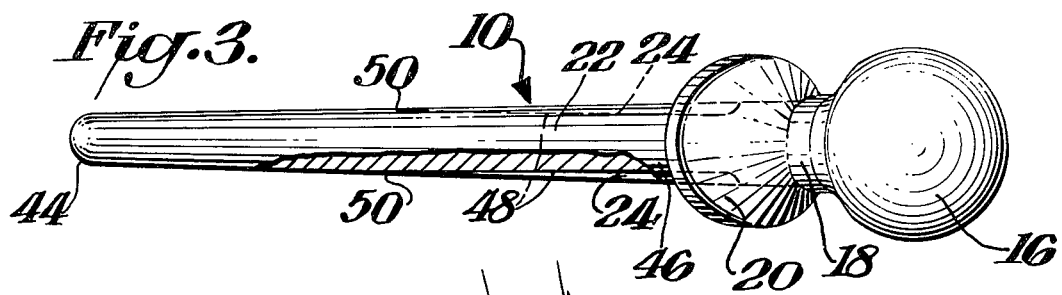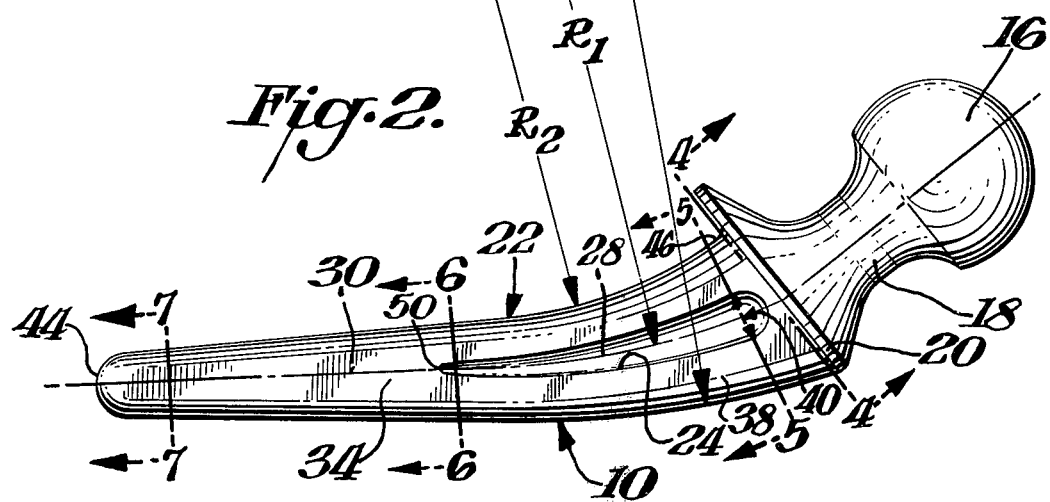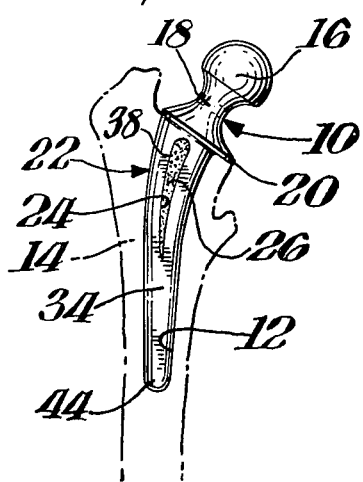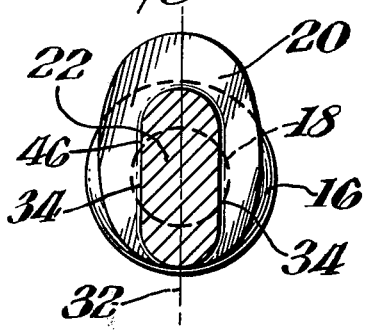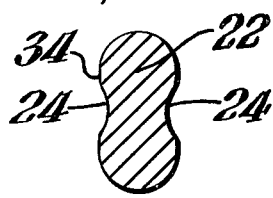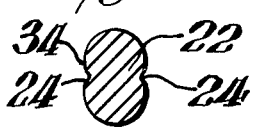

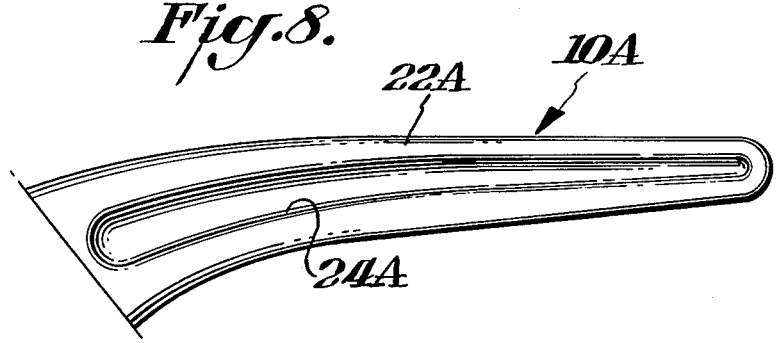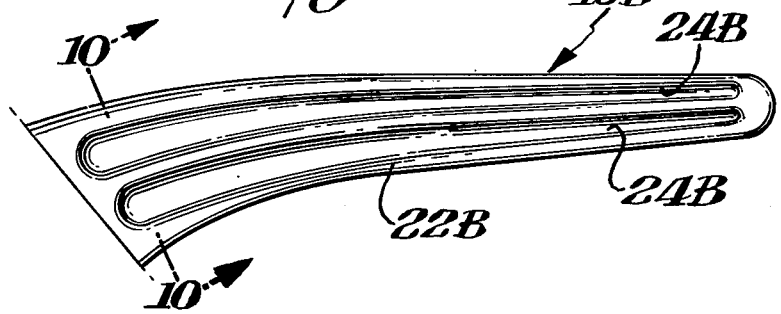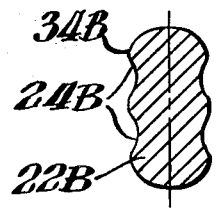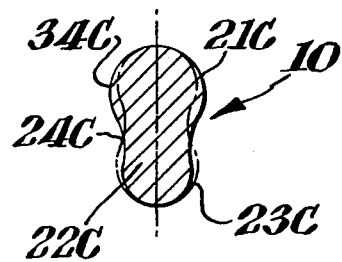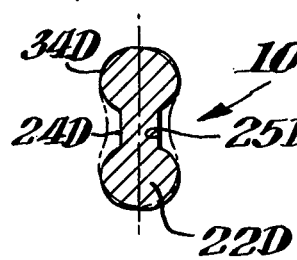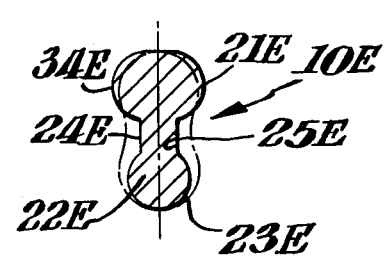

FEMORAL INSERT FOR HIP JOINT PROSTHESIS

CROSS REFERENCE TO RELATED APPLICATIONS

This application is a continuation-in-part of U.S. patent application Ser. No. 523,926, filed Nov. 14, 1974, now abandoned.

BACKGROUND OF THE INVENTION

Femoral inserts used in hip joint prosthesis have a polished spherical head mounted on a stem, which is inserted into the intermedullary canal in the femoral bone. Such inserts are advantageously cemented within the canal to hold them fast against the applied forces and loads. Some of them have utilized cement-holding depressions or cavities, such as those shown in the sides of the hip stem shown in drawing sheet No. 2 of U.S. Pat. No. 3,694,820. Such stems with depressions are not as strong as might be desired and are difficult to remove from the canal within the femoral bone if they must be replaced. An object of this invention is to provide a relatively strong hip stem prosthesis for insertion in the intermedullary canal of a femur which can be rigidly installed and which facilitates removal and replacement.

SUMMARY

In accordance with this invention a femoral insert has a proximally longitudinally curved tapered stem for insertion and cementing within the intermedullary canal of the femur. The stem has substantially flattened ellipsoidal cross section tapering from a relatively high curved proximal portion to a smooth junction with the distal portion which more gradually tapers in height to a rounded end. The thickness of the stem tapers uniformly from the proximal to distal end. One or more shallow teardrop-shaped depressions are disposed in the flat sides of the curved proximal portion of the stem with their bases disposed substantially parallel to each other at a distance apart which smoothly merges into a junction with the outsides of the distal portion and which is not less than the width of the distal end adjacent the tails of the depressions.

BRIEF DESCRIPTION OF THE DRAWINGS

Novel features and advantages of the present invention will become apparent to one skilled in the art from a reading of the following description in conjunction with the accompanying drawings wherein similar reference characters refer to similar parts and in which:

FIG. 1 is a reduced-size side view in elevation of an embodiment of this invention installed within the intermedullary canal of a femur;

FIG. 2 is a side view in elevation of a femoral insert of the embodiment shown in FIG. 1;

FIG. 3 is a top plan view of the embodiment shown in FIG. 2;

FIG. 4 is a cross-sectional view taken through FIG. 2 along the line 4—4;

FIG. 5 is another cross-sectional view taken through FIG. 2 along the line 5—5;

FIG. 6 is still another cross-sectional view taken through FIG. 2 along the line 6—6;

FIG. 7 is a further cross-sectional view taken through FIG. 2 along the line 7—7;

FIG. 8 is a partial side view in elevation of the stem portion of another embodiment of this invention;

FIG. 9 is a side view in elevation of the stem portion of still another embodiment of this invention;

FIG. 10 is a cross-sectional view taken through FIG. 9 along the line 10—10;

FIG. 11 is a cross-sectional view similar to FIG. 10 taken through a further embodiment of this invention whose side view in elevation is similar to FIG. 8;

FIG. 12 is a further cross-sectional view similar to FIG. 10 taken through a further embodiment of this invention whose side view in elevation is similar to FIG. 8; and FIG. 13 is a still further cross-sectional view similar to FIG. 10 taken through a still further embodiment of this invention whose side view in elevation is similar to FIG. 8.

DESCRIPTION OF THE PREFERRED EMBODIMENTS

In FIG. 1 is shown a femoral hip stem component 10 inserted within the intermedullary canal 12 of femur hip bone 14 of a human being. Stem component 10 includes a polished spherical ball 16, which replaces the damaged natural ball in the hip ball and socket joint. Ball 16 is, for example, of the Muller type. Ball 16 is connected by neck 18 and collar 20 to stem 22 which is later described in detail in conjunction with FIG. 2. Stem component 10 also includes a pair of shallow teardrop-shaped depressions 24, which are connected to the walls of the intermedullary canal 12 by cement 26.

FIG. 2 shows the portions of stem component 10 in a larger representation. Stem 22 has a curved proximal axis 28 and a substantially straight distal axis 30, which merge into each other to constitute a bent major axis 28–30 disposed in an axial plane 32 (shown in FIG. 4). Stem 22 has throughout its length substantially ellipsoidal transverse cross-sections shown in FIGS. 4–7, having substantially flat sides 34 disposed substantially parallel to axial plane 32. The ellipsoidal cross-sections shown in FIGS. 4–7 are disposed substantially perpendicular to the bent major axis 28–30 shown in FIG. 2. Each of the flat sides 34 of the curved proximal portion 38 of stem 22 includes a shallow curved teardrop-shaped depression 24 disposed symmetrically about a lateral extension (not specifically shown) of curved proximal axis 28. Depressions 24 taper from a maximum width 40 at its proximal end adjacent collar 20 which is about ⅛ to ¼ of the height of the adjacent proximal portion to a convergent tail at its distal end, which is disposed approximately at the junction between the proximal axis 28 and distal axis 30.

The cross-sections shown in FIGS. 4–7 are an ellipsoidal with substantially flat sides 34 disposed parallel to the axial plane 32. The ellipsoidal cross-sections of FIGS. 4–7 are disposed perpendicular to bent major axis 28–30. The width of stem 22 as shown in elevational view FIG. 2 tapers from a maximum width of about 1 ⅛ inch to a width of about ⅝ inch at the junction of the proximal axis 28 with distal axis 30 to an ultimate height of about ⅜ inch at the rounded tip end 44 of the stem.

The thickness of stem 22 shown in top plan view FIG. 3 tapers uniformly from a maximum dimension at the proximal end 46 of stem 22, which is about ½ inch wide to a width of about 7/16 inch at the junction of the proximal axis 28 with distal axis 30 to an ultimate width at the rounded tip end 44 of stem 22 of about 5/16 inch. FIG. 3 also shows that the substantially parallel bases 48 of depressions 24 are disposed substantially parallel to each other at a distance apart substantially equal to the thickness of the proximal-distal junction section 50 of stem 22. The width defined by bases 48 of depressions 24 and their continuation by the sides of distal portion of the stem slightly tapers inwardly towards the stem at a gradual taper for facilitating insertion and withdrawal of the stem from the canal in the femur. The cross-sections of the stem may also be described as substantially rectangular with rounded upper and lower edges. The proximal portion has substantially flat cross-sections and the distal portion of the stem has more square cross-sections, all with rounded upper and lower ends.

The overall length of the illustrated medium-sized component is approximately 6 inches or 150 mm. with a spherical ball having a diameter of about 1 ¼ inches or 32 mm. The overall length of the stem is about 4.5 inches or 115 mm. The curved proximal portion of the stem may have an axial radius of curvature, $R_1$, of about 5 inches or 127 mm. The corresponding inner radius, $R_2$, of the proximal portion is 2.75 inches or 69.8 mm. and the outer radius, $R_3$, is 7.0 inches or 177.8 mm. There are ellipsoidal cross-sections having substantially flat sides throughout the length of the stem. The height of the proximal portion of the stem tapers from about 1 ¼ inches or 32 mm. to about ⅝ inch or 15 mm. and its junction with the distal portion also ultimately tapers to a rounded tip approximately 0.40 inch or 10.2 mm. high. The width of the proximal portion tapers from about ½ inch or 15 mm. to about ⅜ inch or 10 mm. at its junction with the distal portion, which ultimately tapers to a rounded tail end about 0.30 inch or 7.6 mm. wide. A component for smaller bone sizes has a shorter height at the beginning of the proximal portions just slightly over 1 inch and a lesser axial radius of curvature, $R_1$, of about 3.25 inches or 82.5 mm. The corresponding inner radius of curvature, $R_2$ is 2.5 inches or 63.5 mm. and the outer radius of curvature, $R_3$, is 4.0 inches or 101.6 mm. A pair of teardropshaped depressions in the sides of the curved proximal portion of the stem taper from a width at the proximal end of about 5/16 inch or 7 mm. to a convergent tail which terminates at the junction the proximal and distal portions of the stem. The bases of the teardrop-shaped depressions are disposed substantially parallel to each other at a distance apart which smoothly merges into a junction with the sides of the distal portion. The dimensions may be appropriately varied for larger and smaller bone configuration. The ball sizes also may vary to suit different cups and to suit appropriate bone sizes.

Curved depressions 24 provide extra surfaces and directional configuration, which facilitate retention of component 22 by cement in intermedullary canal 12 in femur bone 14. The unique shape and configuration of stem 24, however, permit its removal without unduly stressing femur 14. The described deposit of depressions 24 in the higher proximal section avoids unduly weakening the stem in a portion where the natural lines of resistant to applied force are concentrated.

The illustrated component 10 can be made by casting in several different sizes, small, medium and large of which the illustrated component is of the medium size. Component 10 is, for example, made of a metal compatible with the human body, such as Vitallium, which is the trademark of a metal by Howmedica Inc. having the following properties.

Vitallium is a special cobalt-chromium alloy developed and used for cast partial and full dentures, and for internal applications by surgeons. Cobalt and chromium constitute over 90% of its composition. Sp.gr. 8.29; tensile strength, 100,000–120,000 lb./sq.in.: yield point, 70,000–80,000 lb./sq.in.: Rockwell "C" hardness, 23–28; elongation, 15–20%; modulus of elasticity in tension, 30,000,000–32,000,000 lb./sq.in. When polished, it is exceedingly smooth and permanently lustrous. Its outstanding qualities are permanently inertness in relation to living tissues, and high degree of resistance to corrosion.

In FIG. 8 is shown a stem portion 22A of hip stem 10A, whose ball portion 16A, neck 18A and collar 20A are omitted but are substantially similar to corresponding elements shown in FIGS. 1–3.

Stem 22A has a teardrop-shaped depression 24A, which is considerably longer than that shown in FIG. 2 and extends almost the entire length of stem 22A. The other aspects of depression 24A are substantially the same as depression 24 shown in FIGS. 1–7, except that depression 24A is slightly wider as well as considerably longer.

The same as above applies to hip stem 10B shown in FIG. 9 except that there are two teardrop-shaped depressions 24B in stem 22B, which are about the same length as depression 24A, but slightly narrower. This pair of depressions 24B provides more cement retention.

The overall width of depressions 24, 24A, 24B, etc. may range approximately from about ⅛ to ¾ of the width of the adjacent portion of the sides 34, 34A, 34B etc. of stems 24, 24A, 24B, etc. to effectively provide adequate cement retention when inserted into the intermedullary canal in the femur bone.

FIGS. 11, 12, 13 show cross-sections taken through still other embodiments of this invention 10C, 10D and 10E in which depressions 24C, 24D and 24E have varying profiles, but still conform with the general shape and specifications of depression 24 shown in FIGS. 1–7 relative to respective stems 22C, 22D and 22E.

Stem 22C accordingly has a wider section 21C disposed towards convex portion of stem 22C than section 23C disposed adjacent the concave portion of stem 22C.

Stem 22D shown in FIG. 12 has a substantially flat base 25D on depression 24D, which accordingly assumes a somewhat trapesoidal shape.

Stem portions 21E and 23E shown in FIG. 13 are similar in relative size of portions 21C and 23C, but depression 24E has a substantially flat base 25E similar to base 25D shown in FIG. 12.

We claim:

1. A femoral insert for a hip joint prosthesis comprising a spherical head, a longitudinally tapered stem adapted for insertion within the femur connected to said spherical head, a neck connected to said spherical head, a collar disposed between said neck and said stem for limiting the insertion of said stem within said femur, said stem having a curved proximal axis and a straight distal axis merging into each other to constitute a bent major axis disposed in an axial plane, said stem having throughout its proximal length substantially ellipsoidal transverse cross-sections with longer sides than widths disposed substantially parallel to said axial plane, said ellipsoidal cross-sections being disposed substantially perpendicular to said bent major axis, at least one curved teardrop-shaped depression disposed symmetrically about a lateral extension of said curved proximal axis in each of said sides, said depression tapering from a maximum width at the proximal end to a convergent tail at the distal end, the proximal and distal sides of said stem tapering in width uniformly from the proximal to distal ends of said stem, and the bases of said curved teardrop-shaped depressions in said sides being disposed substantially parallel to each other at a distance from each other which merges smoothly with the tapering outsides of said distal end and is not less than the width of the distal end adjacent said tail of said depression.

2. A femoral insert as set forth in claim 1 wherein the width of said at least one depression tapers from about ⅓ to ¾ of the width of the adjacent portion of the side to said convergent tail.

3. A femoral insert as set forth in claim 1 wherein only one depression is disposed in each of said sides.

4. A femoral insert as set forth in claim 1 wherein two depressions are disposed in each of said sides.

5. A femoral insert as set forth in claim 1 wherein said sides are substantially flat except for said depressions.

6. A femoral insert as set forth in claim 1 wherein said sides are substantially curved except for said depressions.

7. A femoral insert as set forth in claim 1 wherein said substantially ellipsoidal transverse cross sections are substantially even in size.

8. A femoral insert as set forth in claim 1 wherein said substantially ellipsoidal transverse cross sections are substantially uneven in size.

9. A femoral insert as set forth in claim 1 wherein said substantially ellipsoidal transverse cross sections are substantially uneven in size with the portion adjacent the concave section of the stem being larger than the portion adjacent the convex portion of the stem.

10. A femoral insert as set forth in claim 1 wherein the convergent tail of the depression is disposed substantially at the junction of the proximal and distal portions of the stem.

11. A femoral insert as set forth in claim 1 wherein the convergent tail of the depression is disposed substantially adjacent to the distal portion of the stem.

12. A femoral insert as set forth in claim 1 wherein said insert has an overall length of about 6 inches or 150 mm. and said stem has an overall length of about 4.5 inches or 115 mm.

13. A femoral insert as set forth in claim 12 wherein the proximal end tapers from a maximum height of slightly over 1 inch or 25 mm. to a junction with the distal end of about ⅝ inch or 15 mm.

14. A femoral insert as set forth in claim 13 wherein the depressions have a maximum depth of about 0.010 inch or 2.5 mm.

15. A femoral insert as set forth in claim 14 wherein the distal end of said stem tapers to a junction with the proximal end of said stem to a rounded tail about 0.40 inch high or 10.2 mm. high.

16. A femoral insert as set forth in claim 15 wherein the width of said stem substantially uniformly tapers from about ½ inch or 15 mm. thick to a rounded tail about 0.30 inches or 7.6 mm. wide.

17. A femoral insert as set forth in claim 1 wherein the curved proximal axis comprises an arc of a circle.

18. A femoral insert as set forth in claim 17 wherein the outer and inner surfaces of the curved proximal portion are arcs of circles which merge smoothly into the distal end of the stem.

19. A femoral insert as set forth in claim 1 wherein the collar is substantially elliptical.

20. A femoral insert for a hip joint prosthesis comprising a spherical head, a longitudinally tapered stem adapted for insertion within the femur connected to said spherical head, a neck connected to said spherical head, a collar disposed between said neck and said stem for limiting the insertion of said stem within said femur, said stem having a curved proximal portion and a substantially straight distal portion merging into each other, said proximal portion having a substantially bent cross-section; a pair of curved teardrop-shaped depressions disposed opposite each other in the sides of the proximal portion of the stem, said depressions tapering from a maximum width at the proximal end to a convergent tail near the junction of the proximal and distal ends, and the bases of said curved teardropshaped depressions being disposed substantially parallel to each other at a distance away from each other which merges smooth with the outsides of said distal end of said stem.

21. A femoral insert as set forth in claim 20 wherein the cross-section of said proximal portion is substantially rectangular.

22. A femoral insert as set forth in claim 21 wherein the cross-section of said proximal portion is substantially rectangular with rounded ends.

23. A femoral insert as set forth in claim 22 wherein the cross-section of said proximal portion is substantially ellipsoidal.

24. A femoral insert as set forth in claim 20 wherein said stem has a substantially rectangular cross-section.

25. A femoral insert as set froth in claim 23 wherein the cross-section of said stem is substantially rectangular with rounded ends.

26. A femoral insert as set forth in claim 24 wherein the cross-section of said stem is substantially ellipsoidal.

27. A femoral insert as set forth in claim 20 wherein said proximal portion tapers in height at a ratio of about two to one from its proximal end to its junction with said distal portion.

28. A femoral insert as set forth in claim 27 wherein said proximal portion has inner, outer and axial radii of curvature.

* * * * *